US010766689B2

(12) United States Patent
Buhler et al.

(10) Patent No.: US 10,766,689 B2
(45) Date of Patent: Sep. 8, 2020

(54) PACKAGING FOR TIMEPIECE APPLIQUES

(71) Applicant: Nivarox-FAR S.A., Le Locle (CH)

(72) Inventors: Pierre-Andre Buhler, Orvin (CH); Roger Juillet, Fontainemelon (CH)

(73) Assignee: Nivarox—FAR S.A., Le Locle (CH)

(*) Notice: Subject to any disclaimer, the term of this patent is extended or adjusted under 35 U.S.C. 154(b) by 144 days.

(21) Appl. No.: 15/810,204

(22) Filed: Nov. 13, 2017

(65) Prior Publication Data

US 2018/0170660 A1 Jun. 21, 2018

(30) Foreign Application Priority Data

Dec. 15, 2016 (EP) .................................... 16204370

(51) Int. Cl.

| | |
|---|---|
| ***B65D 85/40*** | (2006.01) |
| ***G04D 1/06*** | (2006.01) |
| ***B65D 81/05*** | (2006.01) |
| ***B65D 21/02*** | (2006.01) |
| ***B65D 1/36*** | (2006.01) |

(Continued)

(52) U.S. Cl.

CPC ............... *B65D 85/40* (2013.01); *B65D 1/36* (2013.01); *B65D 21/0212* (2013.01); *B65D 71/70* (2013.01); *B65D 81/05* (2013.01); *G04D 1/0021* (2013.01); *G04D 1/0071* (2013.01); *G04D 1/066* (2013.01)

(58) Field of Classification Search

CPC ...... B65D 85/40; B65D 1/36; B65D 21/0212; B65D 71/70

USPC ... 206/301, 18, 70, 562, 511, 509, 557–558, 206/563, 566, 564

See application file for complete search history.

(56) References Cited

U.S. PATENT DOCUMENTS 3,902,270 A * 9/1975 Molenaar ............. A63H 33/088 446/122
4,184,592 A * 1/1980 Howard, Jr. ........... B65D 71/70 206/327

(Continued)

FOREIGN PATENT DOCUMENTS

CH 598 082 4/1978
CH 699 057 B1 1/2010

(Continued)

OTHER PUBLICATIONS

European Search Report dated Aug. 8, 2017 in European Application 16204370.7, filed on Dec. 15, 2016 (with English Translation of Categories of cited documents).

*Primary Examiner* — Robert Poon

(74) *Attorney, Agent, or Firm* — Oblon, McClelland, Maier & Neustadt, L.L.P.

(57) ABSTRACT

A packaging for timepiece appliques with a foot and body, including at least one tray provided for the reception, holding, storage and transport of appliques of the same height, including bores for receiving the feet at a constant pitch, adjacent to housings for housing the applique bodies resting on an upper tray surface as opposed to a lower tray surface, each tray including position indexing device, and at least one vertically extending mounting spacer, arranged to cooperate in abutment with a lower surface of another such tray, or a lower spacer surface of a spacer of the packaging, each mounting spacer extending, from the upper tray surface, over a height greater than that of the applique bodies.

13 Claims, 2 Drawing Sheets

(51) Int. Cl.
*B65D 71/70* (2006.01)
*G04D 1/00* (2006.01)

(56) References Cited

U.S. PATENT DOCUMENTS

| | | | | | |
|---|---|---|---|---|---|
| 4,935,208 | A * | 6/1990 | Kohler | B01L 9/52 | 206/558 |
| 5,934,471 | A * | 8/1999 | Jun | B25H 3/06 | 206/509 |
| 6,056,130 | A * | 5/2000 | Ovadia | A47F 7/02 | 206/566 |
| 6,450,341 | B1 * | 9/2002 | Krupa | B65D 5/5038 | 206/497 |
| 7,191,904 | B2 * | 3/2007 | Wescott, III | B01L 9/06 | 206/563 |
| 8,505,723 | B2 * | 8/2013 | Clark | B65D 5/503 | 206/443 |
| 2011/0006059 | A1 * | 1/2011 | Patterson | B65D 71/70 | 220/23.88 |
| 2012/0103861 | A1 * | 5/2012 | Song | A61B 50/33 | 206/563 |
| 2012/0279894 | A1 * | 11/2012 | Lai | B08B 3/047 | 206/557 |

FOREIGN PATENT DOCUMENTS

| | | | |
|---|---|---|---|
| CH | 702 688 | B1 | 8/2011 |
| CH | 706 143 | A2 | 8/2013 |
| CH | 706 143 | B1 | 8/2013 |
| CH | 708 074 | A2 | 11/2014 |
| CH | 708 074 | B1 | 11/2014 |
| EP | 2 455 824 | A1 | 5/2012 |
| EP | 2 455 824 | B1 | 5/2012 |
| EP | 2 799 940 | A1 | 11/2014 |

* cited by examiner

PACKAGING FOR TIMEPIECE APPLIQUES

This application claims priority from European patent application No. 16204370.7 filed on Dec. 15, 2016, the entire disclosure of which is hereby incorporated herein by reference.

Field of the Invention

The invention concerns a packaging for timepiece appliques, said appliques comprising, on either side of a bearing surface, at least one foot, and an applique body extending over an applique height above said bearing surface, said packaging including at least one tray arranged for the reception, holding, storage and transport of said appliques of said same applique height, said tray comprising a series of bores for the reception of said feet at a constant pitch, each said bore being adjacent to a housing arranged for housing one said applique body resting on an upper tray surface as opposed to a lower tray surface.

The invention also concerns an automated means of production for manufacturing such timepiece appliques, said automated means of production including at least one machining unit for profile-turning, and/or milling and/or diamond polishing.

The invention also concerns a method for manufacturing such timepiece appliques.

The invention concerns the field of manufacturing small timepiece display components, in particular appliques, indices, hands, or suchlike.

BACKGROUND OF THE INVENTION

The manufacture of small timepiece display components, such as appliques, indices, hands, or suchlike, is always difficult, as these small-sized components which are difficult to handle without scratching, are visible components which determine, at first glance, the level of finish and quality of a watch or of a timepiece. When such components are made of precious metal, it is important not to lose them among chips or in a treatment or cleaning bath.

CH 702 688 B1 MONYCO discloses a working and handling support for dial index of watch in timepiece field, having fixation unit that fixes sheet to another sheet, and positioning and fixing components that are connected with index to allow positioning of index.

EP 2 455 824 A1 METALEM discloses a method for treating elements intended for being fixed to a watch dial, involving positioning blanks of elements on a support that is configured such that machining operations and surface treatment operations are performed on the blanks mounted on the support, where the support is in form of a disk. The machining operations are performed on surfaces of the blanks of the elements by units cooperating with the blanks mounted on the support. The surface treatment operations are performed on the blanks of the elements mounted on support by electroplating.

EP 2 799 940 A1 SWATCH GROUP MAN SERV AG discloses a packaging for the transport and handling of elongate elements such as watch hands comprising a support having a face known as receiving the elongate elements and means, for fixing said elongate elements, said the fixing means is at least one pad of adhesive material of sufficient height to hold the elongated element at a distance from the receiving face.

SUMMARY OF THE INVENTION

The invention proposes to develop a packaging which, immediately after the initial shaping of small display components for timepieces, generally by machining, but which may also be achieved by casting or three-dimensional printing, ensures the collection of the blanks, the intermediate storage thereof throughout all the manufacturing process operations and the cleaning thereof, these components preferably remaining permanently in the packaging tool according to the invention, once the initial shaping has been carried out.

To this end, the invention concerns a packaging.

The invention also concerns an automated means of production for manufacturing such timepiece appliques, said automated means of production including at least one machining unit for profile-turning and/or milling and/or diamond polishing.

The invention also concerns a method for manufacturing such timepiece appliques.

BRIEF DESCRIPTION OF THE DRAWINGS

Other features and advantages of the invention will appear upon reading the following detailed description, with reference to the annexed drawings, in which.

DETAILED DESCRIPTION OF PREFERRED EMBODIMENTS

Figure 1:
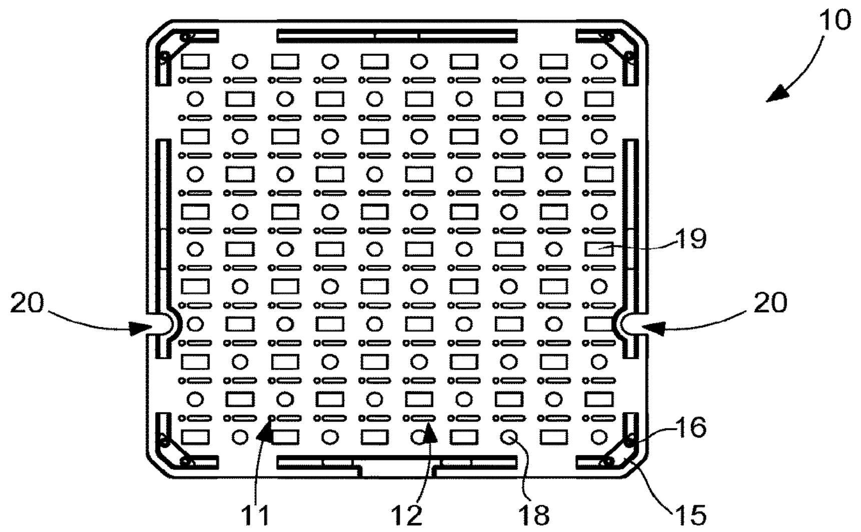
FIG. 1 shows a schematic, front view of a tray constituting a packaging according to the invention.
Figure 2:
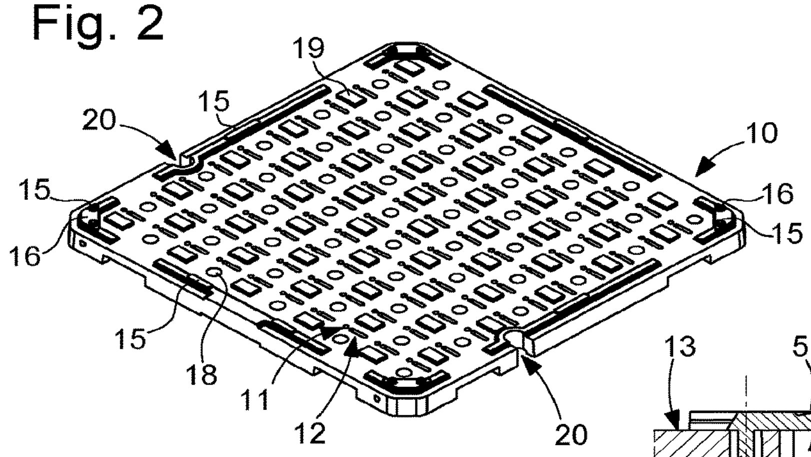
FIG. 2 shows a schematic, perspective view of the tray of FIG. 1.
Figure 3:
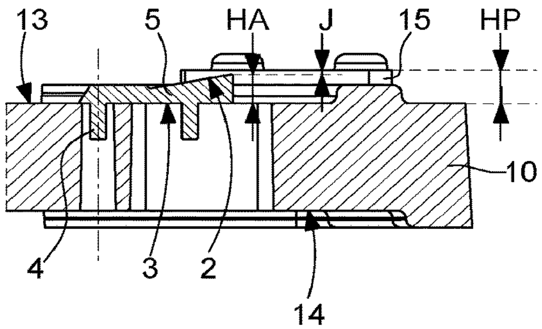
FIG. 3 represents a partial, schematic, cross-section passing through an applique arrangement, of the tray of FIG. 1 in which a timepiece applique is mounted.

The invention proposes to develop a packaging which, immediately after the initial shaping of small display components for timepieces, generally by machining, but which may also be achieved by casting or three-dimensional printing, ensures the collection of the blanks and the intermediate storage thereof throughout all the manufacturing process operations, these components preferably remaining permanently in the packaging tool according to the invention, once the initial shaping has been carried out.

For the sake of simplicity, hereinafter the term "machining operation" will refer to the first shaping operation, whether it is achieved by addition of material (casting, 3D printing, soldering), or by removal of material using a cutting tool (profile-turning and/or milling and/or diamond polishing) or by abrasion (grinding), or both by addition and then removal of material.

The term "applique" will refer to a small display component including at least one foot, such as an applique or index as they are commonly known, or including a pipe instead of a foot, such as a hand.

The invention concerns a packaging 1 for timepiece appliques 2. These appliques 2 comprise, on either side of a bearing surface 3, at least one foot 4, and an applique body 5 extending over an applique height HA above bearing surface 3.

This packaging 1 includes at least one tray 10 provided for the reception, holding, storage and transport of such appliques 2, of the same applique height HA. This tray 10 includes a series of receptacles 11, in particular formed by bores, for the reception of such feet 4, and preferably at a constant pitch. Each receptacle or bore 11 is adjacent to a housing 12, which is arranged to house an applique body 5, resting on an upper tray surface 13, as opposed to a lower tray surface 14.

According to the invention, each tray 10 includes position indexing means 20, for ensuring the precise positioning of the tray with respect to a means of production and/or with respect to a material handling means.

Each tray also includes at least one mounting spacer 15 which extends in a vertical direction (i.e. parallel to the direction of insertion of feet 4 into their receptacles or bores 11), and which is arranged to cooperate in abutment with a lower tray surface 14 of another tray 10, or with a lower spacer surface 34 of a spacer 30 comprised in packaging 1. This spacer 30 is of identical planar dimensions to a tray 10 and it may be necessary in order to hold the components disposed on the top tray 10 in a stack of trays.

Each mounting spacer 15 extends, from the upper tray surface 13, over a tray height HP, which is greater than applique height HA by the value of a predefined operating play J, in particular but not limited to around at least 0.05 mm.

These mounting spacers 15 may be formed of raised edges surrounding tray 10, or discrete protruding portions arranged on its upper surface.

Preferably, packaging 1 includes a plurality of the same trays 10 of identical planar dimensions. Thus, securing such trays in a stack ensures the complete protection of all the components that they carry.

In a particular embodiment illustrated by the Figures, each said tray 10 and/or said spacer 30 is inscribed in a square in each plane perpendicular to said vertical direction.

In a particular variant, allowing precise relative positioning in space of trays 10 in the same stack, or even a snap-fit between neighbouring trays, at least one tray 10 and more particularly each tray in a stack, includes, extending beyond each mounting spacer 15 starting from upper tray surface 13, at least one centring or snap-fit pin 16, which is arranged to cooperate with a centring or snap-fit arrangement 17, and which is comprised in a lower tray surface 14 of another tray 10, or a lower spacer surface 34 of a spacer 30.

Different planar arrangements of the tray may be achieved. In a particular variant, at least one housing 12, or more particularly each housing 12, is separate from the adjacent housings 12. This separation can be achieved by bosses 19, which may in turn constitute mounting spacers 15.

To facilitate production management, in an advantageous variant, at least one, or more particularly each tray 10 and/or spacer 30, includes dimension identification means 50, readable by an automatic, optical, magnetic, inductive, mechanical or other detection means, and/or recognisable by an operator, notably via coloured and/or identification marking; tray 10 may, in particular, be entirely made in a colour allowing it to be identified.

Preferably, at least one, or more particularly each said tray 10 and/or said spacer 30, is entirely made of a material insensitive and resistant to the manufacturing process treatments for appliques 2, for example made of plastic material or a material prepared for this purpose.

In an advantageous variant, at least one, or more particularly each tray 10 and/or spacer 30 includes a plurality of recesses 18 arranged to allow the passage of fluid through its thickness.

In a variant, in at least one, or more particularly each tray 10, every bore 11 is spaced apart from at least one recess 18 by a value lower than or equal to the constant pitch between bores 11.

For secure storage and transport after the applique manufacturing and finishing operations, packaging 1 advantageously includes a case 40, in at least two complementary parts 41 and 42, which together define, in the closed position of case 40, a prismatic chamber 43, whose dimensions are adjusted to receive, with minimum play in the vertical direction, a plurality of trays 10 and/or spacers 30 of the same planar dimensions, and to receive, with minimum play, in each plane perpendicular to the vertical direction, each tray 10 and/or spacer 30.

In a particular variant, this minimum play is zero, case 40 is then made of deformable material, and may even apply a slight clamping force on the trays 10 and spacers 30 that it encloses.

Figure 4:
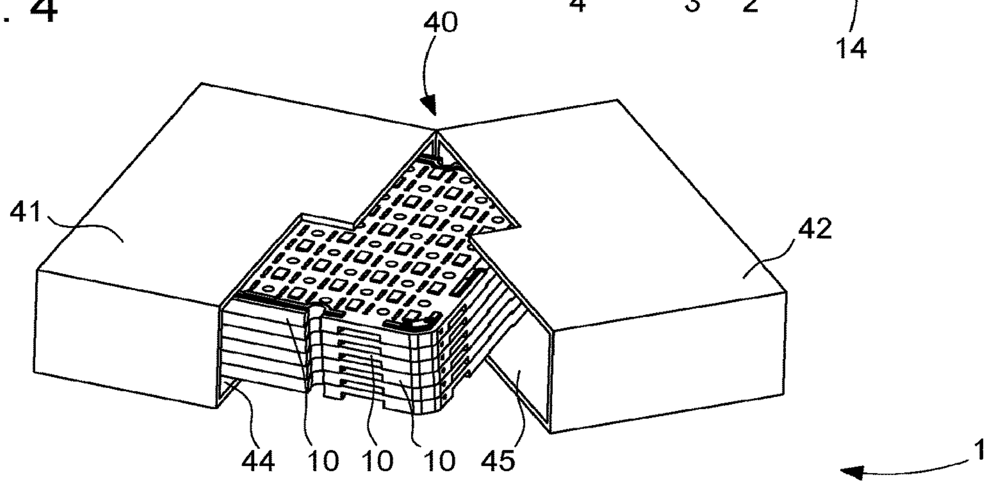
FIG. 4 represents a schematic and perspective view of a case in two parts, comprised in the packaging of the invention, these two parts, which are complementary to each other, each including a half chamber, arranged for the reception of a compact stack of trays according to FIG. 1, possibly supplemented with spacers.
Figure 5:
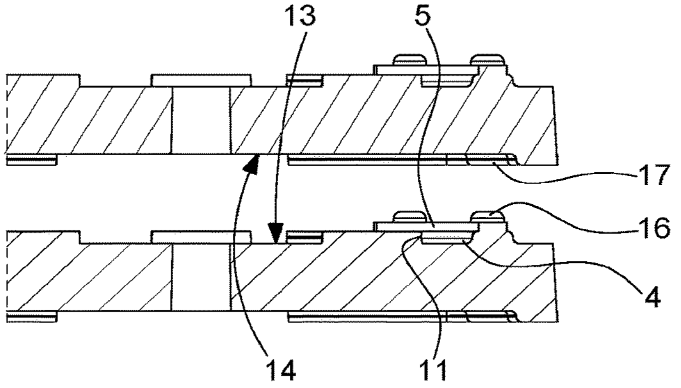
FIG. 5 shows a schematic, partial and cross-sectional view of two superposed trays placed in a position of cooperation.
Figure 8:
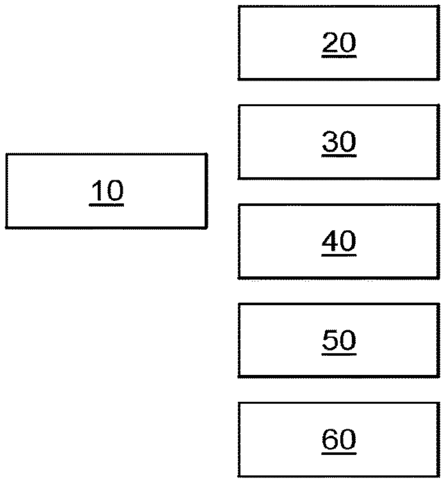
FIG. 8 represents, in the form of a block diagram, the operations of an applique manufacturing method, comprising steps of preparing packagings, preparing raw material, machining, surface treatment, cleaning and inspection.
Figure 6:
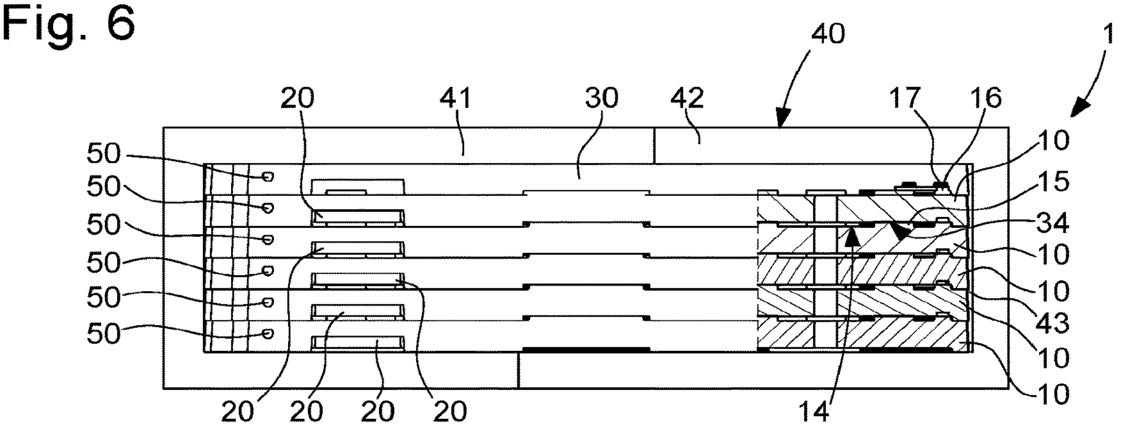
FIG. 6 shows a schematic, partial and cross-sectional view of the case of FIG. 4 containing a secured stack of trays according to FIG. 1, supplemented by an upper spacer to occupy with minimal play all the space of the chamber defined inside this case by the juxtaposition of the two half chambers.
Figure 7:
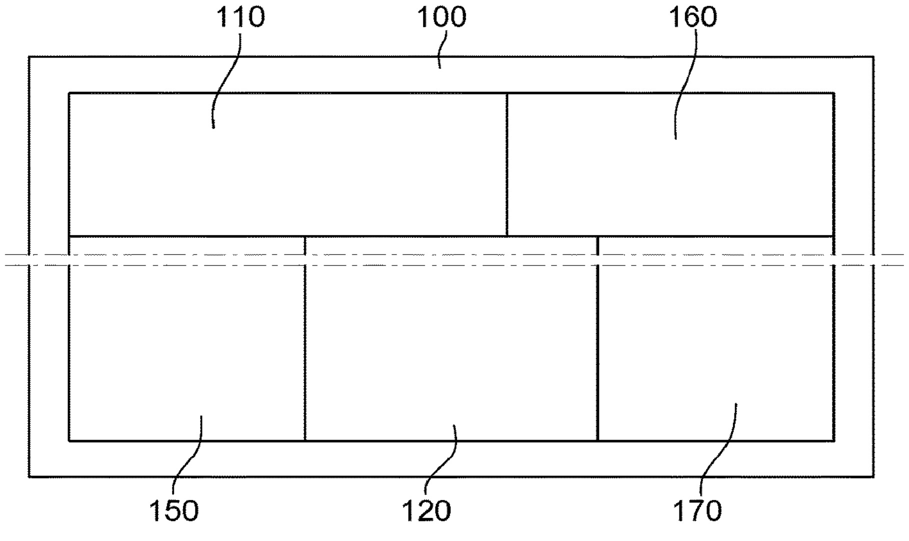
FIG. 7 represents, in the form of a block diagram, an automated means of production that includes, served by a tray loader associated with identification means, a shaping and machining unit, treatment and cleaning equipment, and an inspection and checking unit.

In a particular variant, this case 40 is made of expanded polystyrene, and each of the at least two parts 41, 42 includes a half-chamber 44, 45, arranged to hold alone one stack of trays 10 and/or spacers 30, as seen in FIG. 4.

Case 40 may also be made of another polymer, such as PC, POM, PP, PE, PEHD, PS or suchlike.

The invention also concerns an automated means of production 100 for manufacturing such timepiece appliques 2.

This automated means of production 100 includes at least one initial shaping unit, particularly a machining unit 110 for profile-turning and/or milling and/or diamond polishing.

According to the invention, automated means of production 100 further includes a tray loader mechanism 120, which is arranged to receive and identify a tray 10, arranged for the reception, holding, storage and transport of appliques 2 of the same applique height HA, and which includes position indexing means 20 for the precise positioning of the tray on tray loader mechanism 120.

Advantageously, this tray loader mechanism 120 includes at least one automatic detection means 150, which is arranged to identify the identification means 50 of each tray 10.

In a particular variant, automated means of production 100 includes surface treatment means 160 for the treatment of appliques 2 held positioned in trays 10 after shaping or machining.

In a particular variant, automated means of production 100 includes checking and/or inspection means 170 for the inspection of appliques 2 held positioned in trays 10 after shaping or machining.

The invention also concerns a method for manufacturing such timepiece appliques 2.

According to the invention:

- in a step 10, for each batch of appliques 2 of a given applique height HA, there is provided at least one such packaging 1 adapted to these dimensions;
- in a step 20, there is taken the raw material for use by an automated means of production 100;
- in a step 30, there is performed at least the machining of appliques 2 in an automated means of production 100, which deposits machined appliques 2 in at least one tray 10 of suitable dimensions;
- in a step 50, there is performed at least one cleaning operation on machined appliques 2 in position in their tray 10;
- in a step 60, an inspection is made of appliques 2 in position on their tray 10.

More particularly, after cleaning and prior to final inspection, in a step 40, there is performed on machined appliques 2 held in position on their tray 10 at least one surface treatment and/or coating with a peripheral layer.

In particular, it is possible to make various versions of trays 10, which are distinguished notably by:

- the distance of centres between the feet reception bores, particularly with values comprised between 0.39 mm and 4.08 mm;
- the diameter of these bores, particularly with values comprised between 0.4 mm and 0.6 mm;
- the height of mounting spacers 15 defining the distance between the functional surfaces of two successive trays, to maintain the quality of the applique bodies, particularly with spacing values comprising between 0.42 mm and 1.1 mm;
- the identification means, particularly the colour for fast identification by the preparation operators.

The use of such trays 10 is advantageous, since it allows:

- their immediate use in a machining means, as a result of the tray loader;
- increased autonomy of the machine, sufficiently loaded for one production batch when equipped with one complete tray;
- the cleaning or surface treatment, or heat or other treatment of components directly in the trays;
- the inspection of components directly in the trays.

Indeed, once they leave the production means ensuring their initial shaping, the appliques do not leave the tray, so as to minimise handling costs and maintain as far as possible the aesthetic quality of the product until delivery to the client.

In an economical version, the outer packaging is an expanded polystyrene case 40, devised to close quickly, and to protect several trays at once against shocks during transport. For example, one such case 40 contains around ten trays.

What is claimed is:

1. A packaging, comprising:

timepiece appliques comprising, on either side of a bearing surface, at least one foot, and an applique body extending over an applique height above said bearing surface, a plurality of trays arranged for reception, holding, storage and transport of said appliques of the same said applique height, each tray of said plurality of trays comprising a series of bores extending through the tray and spaced apart by a constant distance, each said bore being adjacent to a housing extending through the tray wherein, for each of said appliques, the at least one foot extends into one of said bores, the applique body extends into an adjacent one of said housings, and the bearing surface rests on an upper tray surface between the one of said bores and the adjacent one of said housings, wherein each said tray includes a plurality of mounting spacers extending in a vertical direction and arranged to cooperate in abutment with a lower tray surface of another tray of said plurality of trays or with a lower spacer surface of a spacer comprised in said packaging and of identical planar dimensions to said tray, each mounting spacer of said plurality of mounting spacers extending, from said upper tray surface, over a tray height greater than said applique height.

2. The packaging according to claim 1, wherein at least one said tray comprises, extending beyond each said mounting spacer of said plurality of mounting spacers, starting from said upper tray surface, at least one centring or snap-fit pin arranged to cooperate with a centring or snap-fit arrangement comprised in a lower tray surface of another tray of said plurality of trays or said lower spacer surface comprised in said spacer.

3. The packaging according to claim 1, wherein each tray of said plurality of trays and said spacer is entirely made of plastic.

4. The packaging according to claim 1, wherein each tray of said plurality of trays and said spacer comprise a plurality of recesses arranged to allow passage of fluid through a thickness of the packaging.

5. The packaging according to claim 4, wherein, for each tray of said plurality of trays, each said bore is spaced apart from at least one said recess by a value lower than or equal to said constant distance.

6. The packaging according to claim 1, wherein said packaging comprises a case, in at least two parts, together defining, in a closed position of said case, a prismatic chamber, whose dimensions are adjusted to receive the plurality of trays and said spacer of the same planar dimensions, and to receive in each plane perpendicular to said vertical direction, each tray of said plurality of trays or said spacer.

7. The packaging according to claim 6, wherein said case is made of expanded polystyrene, and wherein each of said at least two parts comprises a half chamber arranged to hold alone a stack of trays of said plurality of trays.

8. The packaging according to claim 1, wherein each mounting spacer of said plurality of mounting spacers extends by 0.05 mm over said applique.

9. The packaging according to claim 1, wherein a height of each mounting spacer of said plurality of mounting spacers is between 0.42 mm and 1.1 mm.

10. The packaging according to claim 1, wherein a diameter of each of the bores is between 0.4 mm and 0.6 mm.

11. The packaging according to claim 1, wherein a total number of said bores in the packaging is equal to a total number of said housings in the packaging.

12. The packaging according to claim 1, wherein the bore in which said at least one foot is positioned extends completely through the tray directly below where the foot is positioned and wherein the adjacent one of said housings in which the applique body is positioned extends completely through the tray directly below where the applique body is positioned.

13. The packaging according to claim 1, wherein at least one tray of said plurality of trays is arranged such that each of the bores and the adjacent one of said housings are laid out in rows and the rows of the bores and the adjacent one of said housings are separated by a row of recesses arranged to allow passage of fluid through a thickness of the packaging and bosses extending upwardly from a surface of the tray.

* * * * *